US006806304B2

(12) United States Patent
Sanders et al.

(10) Patent No.: US 6,806,304 B2
(45) Date of Patent: Oct. 19, 2004

(54) PROCESS FOR IMPROVING THE SHELF LIFE OF A HINDERED PHENOL ANTIOXIDANT

(75) Inventors: Brent M. Sanders, Stamford, CT (US); Darryl R. Kincaid, Williamstown, WV (US); Sari-Beth Samuels, Mahwah, NJ (US)

(73) Assignee: Cytec Technology Corp., Wilmington, DE (US)

( * ) Notice: Subject to any disclaimer, the term of this patent is extended or adjusted under 35 U.S.C. 154(b) by 34 days.

(21) Appl. No.: 10/128,921

(22) Filed: Apr. 24, 2002

(65) Prior Publication Data

US 2003/0073771 A1 Apr. 17, 2003

Related U.S. Application Data

(60) Provisional application No. 60/325,349, filed on Sep. 27, 2001.

(51) Int. Cl.[7] .................................................. C08L 5/36
(52) U.S. Cl. ........................ 524/303; 524/307; 524/323; 524/351; 524/349
(58) Field of Search ................................ 524/303, 304, 524/305

(56) References Cited

U.S. PATENT DOCUMENTS 3,867,342 A * 2/1975 Guillory et al. ............ 524/305
5,155,153 A * 10/1992 Neri et al. .................. 524/101
5,164,434 A * 11/1992 Liwak et al. ............... 524/100
5,256,488 A * 10/1993 Biggs ......................... 428/463
5,412,012 A * 5/1995 Horwatt et al. ............. 524/265

FOREIGN PATENT DOCUMENTS

GB          963817        *  7/1964

OTHER PUBLICATIONS

Neureiter et al., Ind. Eng. Chem. Prod. Res. Dev., 1962, 14, 236–240.*

* cited by examiner

Primary Examiner—Rip A. Lee
(74) Attorney, Agent, or Firm—James A. Jubinsky; Fran Wasserman; Claire M. Schultz

(57) ABSTRACT

The present invention relates to a process for improving the shelf life of a hindered phenol antioxidant comprising the step of intimately mixing the hindered phenol antioxidant with a sulfur-containing peroxide decomposer. The inventors have discovered that mixing the peroxide decomposer with the hindered phenol antioxidant reduces the tendency of hindered phenols to yellow with age. This increases the desirability of the hindered phenol because it will not impart color to polymer systems. The present invention also relates to a composition produced from the process described above, and stabilized compositions and additive packages containing the composition produced from the above-described process.

14 Claims, No Drawings

PROCESS FOR IMPROVING THE SHELF LIFE OF A HINDERED PHENOL ANTIOXIDANT

This application claims the benefit under 35 U.S.C. § 119(e) of U.S. Provisional Application Ser. No. 60/325,349, filed Sep. 27, 2001.

FIELD OF THE INVENTION

This invention relates generally to a process for improving the shelf life of hindered phenol antioxidants by intimately contacting it with an sulfur-containing peroxide decomposer.

BACKGROUND OF THE INVENTION

Polymers are subject to degradation by environmental forces, such as actinic radiation, oxidation, moisture, atmospheric pollutants and combinations thereof. Degradation, which primarily consists of a change in molecular weight of the polymers, may result in discoloration, brittleness, loss of clarity and mechanical strength, surface crazing and other manifestations.

Antioxidants are often used during the processing of polymers, such as polymer extrusion and molding, to inhibit or retard polymer oxidation and it ensuing degradative effects.

Oxidative degradation of polymers is a sequential process involving initiation, propagation, and termination phases. The initiation phase is started by the formation of free radicals, which may be produced by a number of factors such as the presence of reactive peroxides in the polymerization step, thermal, mechanical and radiation stresses during processing or end-use, or chemical reactions with impurities in the polymer. During the propagation phase, these radicals react with oxygen to form peroxy (ROO.) and alkoxy (RO.) radicals which in turn abstract hydrogen from the polymer to form unstable hydroperoxides (ROOH), alcohols (ROH) and new hydrocarbon free radicals (R.). These free radicals can once again combine with oxygen to continue the oxidative cycle.

Antioxidants can stop this oxidation cycle by interfering with the initiation and propagation steps. Primary antioxidants, such as hindered phenolics and secondary amines, are radical scavengers and react with free, peroxy and alkoxy radicals. Secondary antioxidants, such as phosphites and thioesters, act as peroxide decomposers and react with the unstable peroxides (ROOH) to form more stable alcohols.

One of the problems with some of the hindered phenol primary antioxidants is that they do not have long shelf lives. They tend to yellow with age, which is undesirable because the yellowness imparts color to the polymer. The present invention relates to a process of improving the shelf life of a hindered phenol antioxidant by intimately mixing it with a sulfur-containing peroxide decomposer thereby reducing the yellowness that results from age.

A number of publications, such as U.S. Pat. Nos. 4,820,755; 5,155,153 and 4,579,900, have disclosed the combination of hindered phenol antioxidant and thioesters. However, these patents only disclose the use of these components to stabilize a polymeric composition, and are only mixed together at the time of processing the polymer. There is no disclosure or teaching in these documents on increasing the shelf life of a hindered phenol antioxidant by mixing with a sulfur-containing peroxide decomposer.

SUMMARY OF THE INVENTION

The present invention relates to a process for improving the shelf life of a hindered phenol antioxidant comprising the step of intimately mixing the hindered phenol antioxidant with a sulfur-containing peroxide decomposer. The inventors have discovered that mixing the peroxide decomposer with the hindered phenol antioxidant reduces the tendency of hindered phenols to yellow with age. This increases the desirability of the hindered phenol because it will not impart color to polymer systems.

The present invention also relates to a composition produced from the process described above, and stabilized compositions and additive packages containing the composition produced from the above-described process.

DETAILED DESCRIPTION OF THE INVENTION

The present invention concerns a process for improving the shelf life of a hindered phenol antioxidant comprising the step of intimately mixing the hindered phenol antioxidant with a sulfur-containing peroxide decomposer.

The term "intimately mixing" means that the two components are mixed together so that they are in intimate contact. Examples of such intimate mixing include, but are not limited to at least partially dissolving the two components in a solution, (solution form) or melting one or both components (melt form). The two components are then mixed using any suitable method depending on the form. Although not wishing to be bound by any theory, it appears that there may be a chemical interaction, such as a complex, between the two components, and that they should be in intimate contact in order to improve the shelf life of the hindered phenol antioxidant. In contrast, merely mixing the two components in dry (e.g., powder) form is not intimate mixing because it does not appear to improve shelf life of the hindered phenol antioxidant.

The phrase "improving shelf life" means that the amount of yellowing that occurs in the hindered phenol antioxidant with age is reduced as compared to a hindered phenol antioxidant control that does not contain the sulfide-containing peroxide decomposer. The amount of yellowing that is reduced versus the control preferably is greater than about 5%, or greater than about 10%, or greater than about 20%, or greater than about 30%, or greater than about 50% based on the shelf life testing procedure, (percent transmission (% T) at 420 nm), disclosed in Examples 13 to 24 of the present application. The above percentages can be calculated using the formula—% yellowing reduced=100×((% T sample−% T control)/% T control).

The hindered phenol antioxidants are known compounds used in the polymer industry. Preferably, these compounds contain at least one group of the formula:

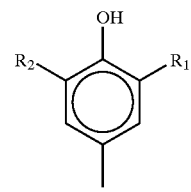

wherein $R_1$ is hydrogen, substituted or unsubstituted alkyl, cycloalkyl, aryl, or araalkyl or substituted thioether having up to 18 carbon atoms and $R_2$ is a substituted or unsubstituted alkyl, cycloalkyl, aryl, or araalkyl or substituted thioether having up to 18 carbon atoms. The above phenolic compound may also be further substituted with additional substituents. Preferably, $R_1$ and $R_2$ are independently methyl or tert-butyl.

Examples of hindered phenol antioxidants include, but are not limited to: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(4,-ethyl-6-tert-butylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α-α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl) dithioterephthalate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate and the calcium salt of monoethyl 3,5-di-tert-butyl-4-hydroxybenzylphosphonate, 2-propenoic acid 2-(1,1-dimethylethyl)-6-[[3-(1,1-dimethylethyl)-2-hydroxy-5-methylphenyl]methyl]-4-methylphenylester, benzene propanoic acid 3,5,-bis(1,1-dimethyl-ethyl)-4-hydroxy-1,6, hexanediylester, benzene propanoic acid 3-(1,-dimethylethyl)-4-hydroxy)-5-methyl-1,2, ethanediylbis(oxy-2,1-ethanediyl)ester, 2,2,-ethylidene-bis-(4,6-ditert-butylphenol, 4,4',4"-(2,4,6-trimethyl-1,3,5-benzenetriyl) tris-(methylene)tris[2,6,-bis(1,1-dimethylethyl)phenol, 1,3,5-tris(3,5-tert-butyl-4-hydroxybenzyl)-s-triazine-2,4,6-(1H, 3H,5H)-trione, octadecyl-3-5-di-tert-butyl-4-hydroxyhydrocinnamate, 1,3,5-tris(4-tert-butyl-3-hydroxy-2-6-dimethylbenzyl)-1,3,5-triazine-2,4,6-(1H,3H,5H)-trione, 1,3,5-trimethyl-2,4,6-tris(3,5-di-tert-butyl-4-hydroxybenzyl)benzene, 2,6-di-tert-butyl-n,d-dimethylamino-p-cresol, 2,2'-oxamido bis-[ethyl 3-(3,5-di-tert-butyl-4-hydroxyphenyl) propionate], 4-methyl-2,6-bis(1-phenylethyl)-phenol, triethyleneglycol-bis-(3-tert-butyl-4-hydroxy-5-methylphenyl) propionate, N,N'-hexamethylene-bis-(3,5-di-tert-butyl-4-hydroxy-hydrocinnamamide), 2,2'-methylene-bis-6-(1-methyl-cyclohexyl)-para-cresol, Benzenepropanoic acid-3,5-bis(1,1-dimethylethyl)-4-hydroxy-C13-15-branched and linear alkyl esters, 2,2'-thiodiethyl bis-(3,5-di-tert-butyl-4-hydroxyphenyl) propionate, tocopherol and mixtures thereof.

A preferred list of phenol antioxidants are 1,3,5-tris(4-tert-butyl-3-hydroxy-2-6-dimethylbenzyl)-1,3,5-triazine-2, 4,6-(1H,3H,5H)-trione, octadecyl-3-5-di-tert-butyl-4-hydroxyhydrocinnamate, 1,3,5-trimethyl-2,4,6-tris(3,5-di-tert-butyl-4-hydroxybenzyl)benzene, 1,1,3-tris(2'-methyl-4'-hydroxy-5'-t-butylphenyl)butane, a compound of the formula:

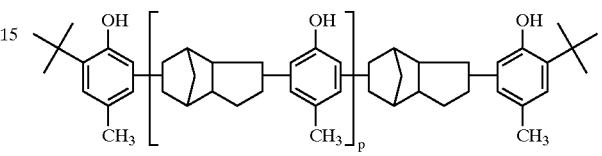

wherein p is an integer of 1 to about 50, and mixtures thereof.

The sulfur-containing peroxide decomposers are also known compounds used in the polymer area. Preferably, these compounds are thioesters. Many thioesters have the formula:

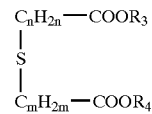

where $R_3$ and $R_4$ are alkyl or alkoxy groups of 1 to about 30 carbon atoms and m and n are integers from 1 to about 10.

Examples of sulfur-containing peroxide decomposers include, but are not limited to: laurylhexylthiodipropionate, dilaurylthiodipropionate, ditridecylthiodipropionate, butylstearylthiodipropionate, 2-ethylhexyllaurylthiodipropionate, di-2-ethylhexylthiodipropionate, diisodecylthiodipropionate, isodecyltetradecylthiodiheptanoate, laurylstearylthiodipropionate, distearylthiodipropionate, hexyltetracosylthiodiacetate, octyltetradecylthiodibutyrate, heptylheptadecylthiodiheptanoate, dimyristyl thiodipropionate, neopentanetetrayl tetrakis(3-dodecylthiopropionate), the 1-lauryl-8-stearyl diester of 4-thiaoctanedioic acid, propanoic acid-3-(dodecylthio)-2,2-bis[3-(dodecylthio)-1-oxopropoxy]methyl-1,3-propanediyl ester, the 1-hexyl-10-tetracosyl diester of 3-thiadecanedioic acid, mercaptobenzimidazole or the zinc salt of 2-mercaptobenzimidazole, zinc alkyldithiocarbamates, zinc dibutyldithiocarbamate, dioctadecyl monosulfide, dioctadecyl disulfide, pentaerythritol tetrakis(β-dodecylmercapto) propionate tetramethyl-thiuram monosulfide, N-cyclohexyl-2-benzothiazolesulfenamide, 2-(morpholinothio) benzothiazole, N-tert-butyl-2-benzothiazolesulfenamide, 2-mercaptobenzothiazole, tetramethylthiuram disulfide, 4,4'dithiodimorpholine and mixtures thereof.

The amount of the sulfur-containing peroxide decomposer is about 0.01% to about 50% by weight based on the total weight of the hindered phenol antioxidant and the sulfur-containing peroxide decomposer. Preferably, the amount of the sulfur-containing peroxide decomposer is about 0.1% to about 30%, about 0.3% to about 20%, about 0.5% to about 15% or about 1% to about 10% by weight based on the total weight of the hindered phenol antioxidant and the sulfur-containing peroxide decomposer.

Preferably, the sulfur-containing peroxide decomposer is intimately mixed with the hindered phenol antioxidant during or just subsequent to the hindered phenol's manufacture. "Just subsequent" means less than about 10 days, or less than about 5 days from the manufacture of the hindered phenol.

The sooner the sulfur-containing peroxide decomposer is mixed with the hindered phenol antioxidant, the better the shelf life. Preferably, the intimate mixing is conducted during the manufacturing process when the hindered phenol may already be in solution form and before it is crystallized and/or dried in solid form.

The dissolution of the two component system in solution form may be conducted in any suitable solvent provided that at least one, and preferably both of the components are at least partially dissolved, and preferably totally dissolved in the solvent. One skilled in the art will be able to choose a suitable solvent.

Similarly, if the two components are mixed in melt form, at least one, and preferably both of the components are at least partially melted, and preferably totally melted when mixed together. One skilled in the art would be able to choose a suitable method such as mixing them in an extruder.

The present invention also contemplates an antioxidant composition produced by the process disclosed above.

This invention further contemplates a stabilized composition containing the two component antioxidant system and a material to be stabilized. Examples of such materials are: polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, styrene acrylonitrile, acrylate styrene acrylonitrile, cellulosic acetate butyrate, cellulosic polymers, polyimides, polyamideimides, polyetherimides, polyphenylsulfides, polyphenylene oxide, polysulfones, polyethersulfones, polyvinylchlorides, polycarbonates, polyketones, aliphatic polyketones, thermoplastic TPO's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, waxes, fibers and mixtures thereof.

The stabilized composition may also contain other additives conventionally employed in the UV stabilizing art such as other anti-oxidants, UV absorbers and stabilizers, metal deactivators, hydroxylamines, nitrones, co-stabilizers, nucleating agents, clarifying agents, neutralizers metallic stearates, metal oxides, hydrotalcites, fillers and reinforcing agents, plasticizers, lubricants, emulsifiers, pigments, rheological additives, catalysts, level agents, optical brighteners, flameproofing agents, anti-static agents and blowing agents.

Examples of these additives may be found, for example, in U.S. Pat. No. 6,096,886, herein incorporated by reference in its entirety. Further examples are those described in Ullmann's Encyclopedia of Industrial Chemistry, 5th Edition, Vol. A18, pp. 429–471, VCH, Weinheim 1991; and Calbo, Leonard J., ed., Handbook of Coatings Additives, New York: Marcel Dekker (1987).

This invention also contemplates an additive package comprising the composition produced by the process above and the other additives conventionally employed in the UV stabilizing art listed above.

Especially preferred additives for the additive package and the stabilized composition are UV stabilizers and other antioxidants including, but not limited to 2-(2'-hydroxyphenyl)benzotriazoles, oxamides, 2-(2-hydroxphenyl)-1,3,5-triazines, 2-hydroxybenzophenones, sterically hindered amines and hindered phenol antioxidants.

Examples of such anti-oxidants and UV stabilizers are: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis($\alpha,\alpha$-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; [R—CH$_2$CH—COO(CH$_2$)$_3$]$_2$ B where R=3'-tert-butyl-4'-hydroxy-5'-2H-benzotrazol-2-ylphenyl; bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazin 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy-4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of β-(3,5-di-tert-butyl-4-hydroxyphenyl)propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

The present invention will now be illustrated by the following examples. The examples are not intended to limit the scope of the present invention. In conjunction with the general and detailed descriptions above, the examples provide further understanding of the present invention.

EXAMPLES

Examples 1 to 12 Preparation of Antioxidant Compositions

Several compositions were prepared using 1,3,5-tris(4-tert-butyl-3-hydroxy-2-6-dimethylbenzyl)-1,3,5-triazine-2,4,6-(1H,3H,5H)-trione (CYANOX® 1790, a trademark of Cytec Industries Inc.) as the hindered phenol antioxidant. A sample of the hindered phenol antioxidant was sampled near the end of its manufacturing process. To approximately a 30% solution of the hindered phenol antioxidant (150 gm) in a methyl isobutyl ketone (MIBK) solvent was added a series of peroxide decomposers as disclosed in Table 1 below. The percent peroxide decomposer added in the Examples is based on the weight of the hinder phenol antioxidant. The mixtures were vacuum distilled and then crystallized using standard methods.

TABLE 1

| Example # | Peroxide decomposer | % Peroxide decomposer |
|---|---|---|
| 1 | None | 0 |
| 2 | Distearylthiodipropionate (CYANOX ® STDP) | 0.3 |
| 3 | STDP | 0.67 |
| 4 | STDP | 1 |
| 5 | STDP | 1.3 |
| 6 | STDP | 1.6 |
| 7 | STDP | 3.3 |
| 8 | STDP | 6.6 |
| 9 | 5-butyl-5-ethyl-2-[2,4,6-tris(1,1-dimethylethyl)-phenoxy]-1,3,2-dioxaphosphorinane (ULTRANOX ® 641) | 1.67 |
| 10 | bis(2,4-di-t-butyl)pentaerythritol diphosphite (ULTRANOX ® 626) | 1.67 |
| 11 | 3,9-bis[2,4-bis(1-methyl-1-phenylethyl)phenoxy]-2,4,8,10-tetraoxa-3,9-diphosphaspiro[5.5]undecane (DOVERPHOS ® S-9228) | 1.67 |
| 12 | tris-(2,4-di-t-butyl phenyl) phosphite (IRGAFOS ® 168) | 1.67 |

ULTRANOX is a trademark of G. E. Specialty Chemicals Inc.
CYANOX is a trademark of Cytec Industries Inc.
DOVERPHOS is a trademark of Dover Chemical Corporation
IRGAFOS 168 is a trademark of Ciba Specialty Chemicals, Corp.

Examples 13 to 24 Shelf Life Testing

The above samples were tested for shelf life. The shelf life tests were performed by placing the samples in a glass container with five holes drilled into the cap for air circulation. The glass containers were then placed in a convection oven at 50° C. for fifty days to accelerate the aging process. The aged samples were then dissolved in toluene for a 23% solution (30 gm sample in 100 gm toluene). The percent transmission, (%T), of the solution was measured at a wavelength of 420 nm as an indication of yellowness. The higher the percent transmission, the less yellowing and the greater the improvement in shelf life.

TABLE 2

| Example # | Preparation Example | % peroxide decomposer | Percent transmission (% T) |
|---|---|---|---|
| 13 | 1-Control | 0 | 51.5 |
| 14 | 2-Sulfur | 0.3 | 53 |
| 15 | 3-Sulfur | 0.67 | 64 |
| 16 | 4-Sulfur | 1 | 75 |
| 17 | 5-Sulfur | 1.3 | 81 |
| 18 | 6-Sulfur | 1.6 | 80 |
| 19 | 7-Sulfur | 3.3 | 82 |
| 20 | 8-Sulfur | 6.6 | 91.5 |
| 21 | 9-Phosphite | 1.67 | 35 |
| 22 | 10-Phosphite | 1.67 | 17 |
| 23 | 11-Phosphite | 1.67 | 53 |
| 24 | 12-Phosphite | 1.67 | 46 |

The results demonstrate that the sulfur-containing peroxide decomposer decreased the amount of yellowing thereby improving the shelf life of the hindered phenol antioxidant. Surprisingly, the compositions containing the phosphite-based peroxide decomposers were similar, or had more yellowing than the control.

Comparison Example C-25—Shelf Life Testing Without Intimate Mixing

A comparison sample, C-25, was prepared to determine if physically mixing powders of the hindered phenol antioxidant and sulfur-containing peroxide decomposer would lead to a reduction of yellowing with age. The components, STDP and CYANOX 1790, were physically dry blended. The blend was then shelf life tested using the procedure in Examples 13 to 24 above. The result is shown in Table 3 below.

TABLE 3

| Example | % peroxide decomposer | Percent transmission (% T) |
|---|---|---|
| C-25 | 5.25 | 48.5 |

This data shows that physical dry blending of the components does not result in an improvement in shelf life.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A process for improving the shelf life of a hindered phenol antioxidant comprising the step of intimately mixing said hindered phenol antioxidant with a sulfur-containing peroxide decomposer selected from a thioester, wherein said intimate mixing is performed during or just subsequent to the manufacture of said hindered phenol antioxidant.

2. The process of claim 1 wherein said hindered phenol antioxidant contains at least one group of the formula:

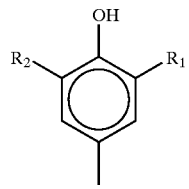

wherein R is hydrogen, substituted or unsubstituted alkyl, cycloalkyl, aryl, or araalkyl or substituted thioether having up to 18 carbon atoms, and $R_2$ is a substituted or unsubstituted alkyl, cycloalkyl, aryl, or araalkyl or substituted thioether having up to 18 carbon atoms.

3. The process of claim 1 wherein $R_1$ and $R_2$ is independently methyl or tert-butyl.

4. The process of claim 1 wherein said hindered phenol antioxidant is selected from the group consisting of: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(4,-ethyl-6-tert-butylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α-α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl)dithioterephthalate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate and the calcium salt of monoethyl 3,5-di-tert-butyl-4-hydroxybenzylphosphonate, 2-propenoic acid 2-(1,1-dimethylethyl)-6-[[3-(1,1-dimethylethyl)-2-hydroxy-5-methylphenyl]methyl]-4-methylphenylester, benzene propanoic acid 3,5,-bis(1,1-dimethylethyl)-4-hydroxy-1,6, hexanediylester, benzene propanoic acid 3-(1,-dimethylethyl)-4-hydroxy)-5-methyl-1,2,ethanediylbis(oxy-2,1-ethanediyl)ester, 2,2,-ethylidene-bis-(4,6-ditertbutylphenol, 4,4',4"-(2,4,6-trimethyl-1,3,5-benzenetriyl) tris-(methylene) tris[2,6,-bis(1,1-dimethylethyl)phenol, 1,3,5-tris(3,5-tert-butyl-4-hydroxybenzyl)-s-triazine-2,4,6-(1H, 3H,5H)-trione, octadecyl-3-5-di-tert-butyl-4-hydroxyhydrocinnamate, 1,3,5-tris(4-tert-buty -hydroxy-2-6-dimethylbenzyl)-1,3,5-triazine-2,4,6-(1H,3H,5H)-trione, 1,3,5-trimethyl-2,4,6-tris(3,5-di-tert-butyl-4-hydroxybenzyl)benzene, 2,6-di-tert-butyl-n,d-dimethylamino-p-cresol, 2,2'-oxamido bis-[ethyl 3-(3,5-di-tert-butyl-4-hydroxyphenyl) propionate], 4-methyl-2,6-bis(1-phenylethyl)-phenol, triethyleneglycol-bis-(3-tert-butyl-4-hydroxy-5-methylphenyl) propionate, N,N'-hexamethylene-bis-(3,5-di-tert-butyl-4-hydroxy-hydrocinnamamide), 2,2'-methylene-bis-8-(1-methyl-cyclohexyl)-para-cresol, C13-15-branched or linear alkyl esters of 3,5-bis(1,1-dimethylethyl)-4-hydroxybenzenepropanoic acid, -2,2'-thiodiethyl bis-(3,5-di-tert-butyl-4-hydroxyphenyl) propionate, tocopherol and mixtures thereof.

5. The process of claim 1 wherein said hindered phenol antioxidant is selected from the group consisting of: 1,3,5-tris(4-tert-butyl-3-hydroxy-2-6-dimethylbenzyl)-1,3,5-triazine-2,4,6-(1H,3H,5H)-trione, octadecyl-3-5-di-tert-butyl-4-hydroxyhydrocinnamate, 1,3,5-trimethyl-2,4,6-tris(3,5-di-tert-butyl-4-hydroxybenzyl)benzene, 1,1,3-tris(2'-methyl-4'-hydroxy-5'-t-butylphenyl)butane, a compound of the formula:

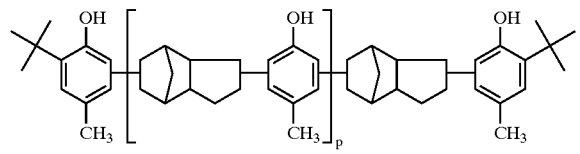

wherein p is an integer of 1 to about 50, and mixtures thereof.

6. The process of claim 1 wherein said thioester has the structure:

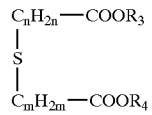

wherein $R_3$ and $R_4$ are alkyl or alkoxy groups of 1 to about 30 carbon atoms and m and n are integers from 1 to about 10.

7. The process of claim 1 wherein said sulfur-containing peroxide decomposer is selected from the group consisting of: laurylhexylthiodipropionate, dilaurylthiodipropionate, ditridecylthiodipropionate, butylstearylthiodipropionate, 2-ethylhexyllaurylthiodipropionate, di-2-ethylhexylthiodipropionate, diisodecylthiodipropionate, isodecyltetradecylthiodiheptanoate, laurylstearylthiodipropionate, distearylthiodipropionate, hexyltetracosylthiodiacetate, octyltetradecylthiodibutyrate, heptylheptadecylthiodiheptanoate, dimyristyl thiodipropionate, neopentanetetrayl tetrakis(3-dodecylthiopropionate), the 1-lauryl-8-stearyl diester of 4-thiaoctanedioic acid, propanoic acid-3-(dodecylthio)-2,2-bis[3-(dodecylthio)-1-oxopropoxy]methyl-1,3-propanediyl ester, the 1-hexyl-10-tetracosyl diester of 3-thiadecanedioic acid.

8. The process of claim 1 wherein said sulfur-containing peroxide decomposer is selected from the group consisting of: laurylstearylthiodipropionate, dilaurylthiodipropionate, ditridecylthiodipropionate, distearylthiodipropionate, propanoic acid-3-(dodecylthio)-2,2-bis[3-(dodecylthio)-1-oxopropoxy]methyl-1,3-propanediyl ester and mixtures thereof.

9. The process of claim 1 wherein said intimate mixing is accomplished by contacting said hindered phenol antioxidant with said sulfur-containing peroxide decomposer in a solution.

10. The process of claim 1 wherein said intimate mixing is accomplished by contacting said hindered phenol antioxidant with said sulfur-containing peroxide decomposer in a melt.

11. The process of claim 1 wherein the amount of said sulfur-containing peroxide decomposer is about 0.01% to about 50% by weight, based on the total weight of said hindered phenol antioxidant and said sulfur-containing peroxide decomposer.

12. The process of claim 1 wherein the amount of said sulfur-containing peroxide decomposer is about 0.3% to about 20% by weight, based on the total weight of said hindered phenol antioxidant and said sulfur-containing peroxide decomposer.

13. A composition produced by the process of claim 1.

14. A process for improving the shelf life of a hindered phenol antioxidant comprising the step of mixing said hindered phenol antioxidant with a sulfur-containing peroxide decomposer thereby improving the shelf life of said hindered phenol antioxidant.

* * * * *

UNITED STATES PATENT AND TRADEMARK OFFICE
CERTIFICATE OF CORRECTION

PATENT NO. : 6,806,304 B2
DATED : October 19, 2004
INVENTOR(S) : Brent M. Sanders, Darryl R. Kincaid and Sari-Beth Samuels It is certified that error appears in the above-identified patent and that said Letters Patent is hereby corrected as shown below:

Column 10,
Line 10, the text reading "wherein Ris" should read -- $R_1$ is --; and
Line 15, the text reading "claim 1" should read -- claim 2 --.

Column 11,
Line 5, the text reading "1,3,5-tris(4-tert-buty –hydroxy" should read -- 1,3,5-tris(4-tert-butyl-3-hydroxy --.
Line 14, the text reading "2,2'-methylene-bis-8" should read -- 2,2'-methylene-bis-6 --.
Line 15, the text reading "C13-15-branched" should read -- $C_{13-15}$-branched --.
Line 45, the text reading "wherein $R_3$ and $R_4$ are alkyl or alkoxy groups" should read -- wherein $R_3$ and $R_4$ are independently alkyl groups --.

Column 12,
Line 46, the text reading "decomposer thereby improving the shelf life of said" should read -- decomposer during the manufacture of said --.

Signed and Sealed this

First Day of February, 2005

JON W. DUDAS
*Director of the United States Patent and Trademark Office*